United States Patent [19]

Cozens et al.

[11] 4,238,422
[45] Dec. 9, 1980

[54] SUBSTITUTED PHENYL PHOSPHINITES AND PHOSPHONITES

[75] Inventors: Ross J. Cozens, Mossley Hill; James R. Jennings, Hutton Rudby; Philip J. Hogan, Runcorn, all of England; Lawrence F. M. Kelly, Canberra, Australia

[73] Assignee: Imperial Chemical Industries Limited, London, England

[21] Appl. No.: 58,543

[22] Filed: Jul. 17, 1979

[30] Foreign Application Priority Data

Jul. 26, 1978 [GB] United Kingdom ............... 31148/78

[51] Int. Cl.³ ............................ C07F 9/46; C07F 9/48
[52] U.S. Cl. .................................. 260/945; 260/944; 260/951; 260/962; 260/465.8 D
[58] Field of Search ................ 260/962, 465.8 D, 945, 260/951, 944

[56] References Cited

U.S. PATENT DOCUMENTS

| | | | |
|---|---|---|---|
| 4,102,915 | 7/1978 | Jennings et al. | 260/465.8 D |
| 4,126,632 | 11/1978 | Hogan et al. | 260/465.8 D |
| 4,129,587 | 12/1978 | Jennings et al. | 260/465.8 D |
| 4,138,428 | 2/1979 | Jennings et al. | 260/962 X |

OTHER PUBLICATIONS

Ugo, "Aspects of Homogeneous Catalysis", vol. 2, Chapter 4, pp. 159-188, (1974).

Primary Examiner—Anton H. Sutto
Attorney, Agent, or Firm—Cushman, Darby & Cushman

[57] ABSTRACT

Novel phosphinites and phosphonites of general formula:

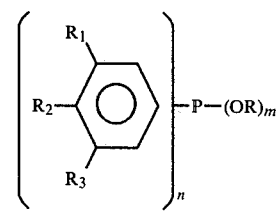

where $R_2$ is an electron-donating substituent, $R_1$ and $R_3$ are electron-donating substituents or hydrogen atoms, provided that they are not both hydrogen atoms, or either $R_1$ or $R_3$ forms part of a fused alicyclic ring with $R_2$, R is alkyl or cycloalkyl, and n and m are integers, each being either 1 or 2, provided that (m+n) equals 3, and when n is 2, the substituents on each aromatic ring may be the same or different, and their use as catalysts for the dimerisation of acrylonitrile to give predominantly straight-chain $C_6$ dimers.

9 Claims, No Drawings

SUBSTITUTED PHENYL PHOSPHINITES AND PHOSPHONITES

This invention relates to novel organo-phosphorus compounds, especially to novel phosphonites and phosphinites, to methods for their preparation and to their use as catalysts in the dimerisation or acrylonitrile.

Oligomerisation and dimerisation of acrylonitrile to branched product by the action of phosphines in protonic solvents has been known for some time. Phosphine catalysed dimerisation to low yields of linear dimer was later achieved by optimisation of catalyst type, protonic solvent and operating temperature. For a comprehensive survey of these developments, see "Dimerisation of Acrylic Compounds" by Masanobu Hidai and Akira Misono, Chapter 4 in "Aspects of Homogeneous Catalysis" ed. R. Ugo (D Deidel, 1974).

In our copending British applications Nos. 45324/75 and 52888/75 (published as German OLS No. 2649904) we describe and claim a process for the dimerisation of acrylonitrile to predominantly straight-chain $C_6$ dinitriles, in which the acrylonitrile is contacted with an organic phosphorus (III) compound which has at least one hydrocarbyl and at least one alkoxy or cycloalkoxy group attached to the phorphorus atom or atoms, the acrylonitrile being dissolved in an organic solvent, capable of donating protons, for example, a hydroxylic solvent such as an alcohol, the acrylonitrile and solvent being substantially dry.

Furthermore, in our co-pending British patent application No. 15029/77 (published as German OLS No. 2747139) we describe a modification of the above process in which the phosphorus compound catalyst is one having a formula:

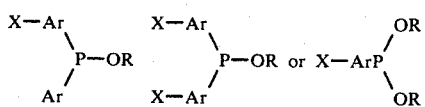

where R represents a hydrocarbyl group, Ar represents an aromatic nucleus and groups X are electron-donating substituents which give rise to a negative Hammett $\sigma$ constant. Suitable substituents include alkoxy, dialkylamino and alkylamino groups. The use of the above-mentioned substituted aryl phosphorus compounds, namely phosphinites or phosphonites, give rise to an enhanced rate of dimer formation.

We have now found alternative novel phosphinites and phosphonites which may advantageously be used in the dimerisation of acrylonitrile.

According to the present invention, we provide, as new compounds, phosphinites and phosphonites of general formula:

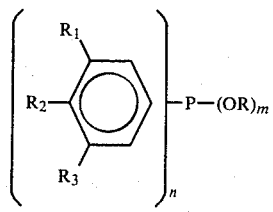

where $R_2$ is an electron-donating substituent, $R_1$ and $R_3$ are electron-donating substituents or hydrogen atoms, provided that they are not both hydrogen atoms, or either $R_1$ or $R_3$ forms part of a fused alicyclic ring with $R_2$, R is alkyl or cycloalkyl, and n and m are integers, each being either 1 or 2, provided that (m+n) equals 3, and when n is 2, the substituents on each aromatic ring may be the same or different.

By "electron-donating substituent" we mean a substituent of the aromatic nucleus which gives rise to a negative Hammett $\sigma$ constant.

A discussion on Hammett $\sigma$ constants and a table showing values for most common substituents is to be found in an article by Clark and Perrin in Quarterly Reviews, vol 18, 1964, pp 295–320.

Examples of suitable substituents $R_1$, $R_2$, $R_3$ include alkoxy groups, e.g. methoxy, ethoxy, i-propoxy and t-butoxy; alkyl groups, e.g. methyl, ethyl and propyl; and alkyl amino groups, e.g. dimethylamino and diethylamino. The alkoxy, alkyl and alkylamino groups preferably contain from 1 to 8 carbon atoms, especially from 1 to 5 carbon atoms. It is essential that groups $R_1$, $R_2$, $R_3$ should be those which do not react adversely with the components of the reaction system.

Suitable groups R include alkyl groups such as methyl, ethyl, isopropyl, neopentyl, 2-ethylhexyl; and cycloalkyl groups such as cyclohexyl.

There is no finite limit on the numbers of carbon atoms which group R may contain; but it will commonly contain from 1 to 10 carbon atoms. When two groups R are present, they may be the same or different; but, generally they will be the same.

The compounds of the present invention may be prepared by any suitable technique for the preparation of organo-phosphorus compounds, such as those detailed in "Organo-Phosphorus Compounds," by Kosolapoff and Maier, published by Wiley 1972, Volume 4, Chapters 10 and 11.

The above-mentioned compounds may be prepared by the action of a Grignard reagent on a suitably substituted phosphorus halide in an appropriate solvent, for example, tetrahydrofuran. For example, a 3,4-dialkylphenyl magnesium bromide or a 4-dialkylamino phenyl magnesium bromide may be reacted with a phosphorhalidite, prepared by reacting a phosphorus halide with the apropriate alcohol. It will be appreciated that to prepare phosphinites a phosphormonohalidite must be used, whereas phosphonites are prepared from a phosphordihalidite.

Another convenient and economical route for the preparation of many of the compounds of our invention comprises, for example, reacting 1,2,3-trimethyl benzene, o-xylene or tetralin with a phosphorus trihalide, in the presence of a Friedel-Crafts catalyst to form the appropriate phosphonous dihalide and then either alcoholising the dihalide to form a phosphonite or heating the dihalide with a catalyst, for example anhydrous zinc chloride, to form the phosphinous monohalide, with evolution of phosphorus trihalide, and then alcoholising the monohalide to form a phosphinite.

In any of the above processes the products are recovered as colourless or pale-coloured oils which may be purified by fractional distillation.

The compounds of our invention may be used as catalysts for the dimerisation of acrylonitrile by the process described and claimed in our copending UK patent applications Nos. 45324/75, 52888/75 and 19108/76.

In such a process the acrylonitrile, substantially free of water and acrylonitrile stabilisers of the phenolic type, e.g. hydroquinone, is contacted with the phosphinite or phosphonite catalyst, the acrylonitrile being dissolved in an inert organic solvent which is capable of donating protons.

By an "inert" solvent, we mean one which is substantially unreactive with respect to addition to, or reaction with, the unsaturated linkage of the acrylonitrile or the products of the acrylonitrile dimerisation. Furthermore, the solvents must not react with the phosphorus compound or catalytic intermediates to form inactive phosphorus species at such a rate as to seriously impair the dimerisation reaction.

Preferably hydroxylic solvents, such as alcohols, are used, provided always that they do not react adversely with the phosphorus compound or any intermediates it may form with acrylonitrile. This may be readily established by experiment. Tertiary and secondary alcohols are preferred, for example, t-butylalcohol, 2-butanol and isopropanol.

The concentration of proton-donating solvent is generally in the range 5 to 50% by volume, calculated on the total volume of the reactants, but the optimum concentration will vary with the precise nature of the solvent and the catalyst compound. The molar concentration of proton-donating solvent will generally be greater than the molar concentration of the phosphorus (III) compound.

In order to reduce the amount of hexamer and/or other oligomers or polymers (hereafter referred collectively as polymeric by-products or merely polymers) which may be co-produced with the desired dimeric products, it is often desirable to add an inert, non-hydroxylic co-solvent to the reaction mixture used in our process. It will be apparent that the co-solvent must be dried to a level which maintains the overall anhydrous state of the system.

Suitable non-hydroxylic organic solvents include hydrocarbons, for example, hexane, cyclohexane, toluene, and petroleum ethers; ethers, for example, tetrahydrofuran, diethyl ether and di-isopropyl ether; and nitriles, for example, acetonitrile, propionitrile; and fluorobenzenes. The hydrocarbon co-solvents are generally preferred; but in any event the solvent should be chosen to give a homogeneous medium.

An essential feature of the present invention is that the reaction must be conducted in the substantial absence of water. Without prejudice to our invention, we believe that the water reacts with the catalyst in the presence of acrylonitrile to give non-catalytic addition compounds. Thus, the acrylonitrile, proton-donating solvent and co-solvent must be dried before use, otherwise the reaction may be completely inhibited. In particular acrylonitrile, which commonly contains as much as 4000 ppm of water, even after distillation, must be rigorously dried. It is also noted that hydroquinone stabilisers, which are present in acrylonitrile as supplied, should be removed. For example, if the reactants contain 300 ppm of water, reaction is seriously inhibited at a concentration of the phosphorus compound of 0.5% by volume; but at water concentrations of 50 ppm or lower reaction takes place readily. Any suitable drying technique may be used, provided that the final water level is sufficiently low. For example, acrylonitrile and hydroxylic solvents may be dried by being contacted with the calcium hydride or a 3A or 4A molecular sieve. The above findings contrast strongly with the teaching of the prior art which makes no mention of removal of water and/or hydroquinone stabilisers, and in many instances advocates the addition of water and stabilisers, such as hydroquinone, to the reaction mixture. It will be appreciated that at higher concentration of water, e.g. 300 ppm, it may be possible to cause the reaction to proceed by adding much larger amounts of catalyst. If this is done, selectivity is generally unaffected, but the process would become commercially unattractive because of high catalyst usage.

The concentration of acrylonitrile in the solvent or solvent mixture generally should range from 5 to 75% by volume. The concentration of acrylonitrile is kept as high as possible in order to optimise throughput and thus concentrations in the range 10 to 50% by volume are generally preferred.

The concentration of the phosphorus compound in the reactant mixture may be varied over a wide range, for example, from 0.001, commonly 0.1, to 5% by volume, calculated on the volume of liquid reactants; but preferably the concentration is in the range 0.1 to 3% by volume. When present, the proportion of co-solvent in the reaction mixture may be varied over wide limits. In general the ratio of proton-donating solvent to co-solvent is in the range 1:20 to 20:1, commonly in the range 1:9 to 9:1, but the ratios outside these limits may be used. Conveniently the said ratio is in the range 1:2 to 2:1, for example about 1:1. However the final choice of ratio will depend on how it is desired to run the process and the choice of catalyst compound.

The reaction temperature is commonly in the range 0° to 120° C.; but it is generally preferred to keep the range temperature below 75° C. to minimise polymerisation of the acrylonitrile and dimeric products. Preferably, the reaction temperature is in the range 20° to 70° C. It is noted that the reaction will proceed below 0° C., maintaining selectivity, but at a reduced rate.

Unlike other acrylonitrile dimerisation processes, the presence of compounds such as hydroquinone and its monomethyl ether, p-methoxphenol, which are commonly used at present as acrylonitrile stabilisers, should be avoided.

The reaction may be carried out batchwise or continuously. In the latter case it may be convenient to support the catalyst compound or to use a polymeric tervalent phosphorus compound to enable the reaction to be carried out in the liquid phase using a heterogeneous catalyst.

The dimeric products of our invention are predominantly linear $C_6$ dinitriles, especially the 1,4-dicyanobutenes. Selectivities >90 wt % (calculated on total dimeric product) may be readily obtained and selectivities as high as 98% have been obtained using our most advantageous catalysts.

The desired products may be readily separated from the reaction mixture for example by fractional distillation or solvent extraction.

The invention will be illustrated by the following Examples.

All operations in the following Examples were carried out under a dry, inert atmosphere, using carefully dried equipment.

EXAMPLE 1

Preparation of Isopropyl bis(3,4-dimethylphenyl) Phosphinite (Friedel-Crafts Route)

(a) Preparation of 3,4-dimethylphenyl phosphonous dichloride

A mixture of carefully dried o-xylene (29.9 g), freshly prepared anhydrous aluminium trichloride (56 g) and freshly distilled phosphorus trichloride (172.6 g) was refluxed gently, with stirring, for 2 hours. The mixture was then refluxed vigorously for a further 1½ hours. The source of heat was removed and freshly distilled phosphoryl chloride (64.5 g) added to the mixture dropwise, with stirring, so that reflux was maintained; a white solid precipitated during the addition. The reaction mixture was allowed to cool to room temperature and dry pentane (100 ml) was added and the resultant mixture stirred for several hours, after which the precipitated solids were filtered off and washed with dry pentane. Volatile products were removed from the combined filtrates under reduced pressure, and the resulting yellow oil was fractionally distilled under reduced pressure. The required product 3,4-dimethylphenyl phosphonous dichloride (58 g) was distilled at a pressure of 0.05 mmHg at 78°–80° C. This was equivalent to a yield of 65.6% based on o-xylene. It was a colourless liquid.

(b) Preparation of bis(3,4-dimethylphenyl) phosphinous monochloride

A mixture of 3,4-dimethylphenyl phosphonous dichloride (37.6 g) and freshly prepared anhydrous zinc chloride (1.96 g) was heated at 280°–320° C. in a distillation apparatus which incorporated a heated fractionating head, maintained at 120° C. The reaction was carried out under a reduced pressure of approximately 200 mmHg for a period of 5 hours. Phosphorus trichloride (12.4 g) was evolved during the reaction and was trapped out using liquid nitrogen. The reaction mixture was then fractionally distilled under reduced pressure by increasing the vacuum. Unreacted starting material was distilled off, as a colourless liquid, at 70°–125° C. at 0.05 mmHg pressure. Product bis(3,4-dimethylphenyl) phosphinous monochloride, was then distilled, as a colourless liquid, at 130°–155° C. and a pressure of 0.05 mmHg. The product weighed 12.5 g, equivalent to a yield of 56.7% based on a conversion of 87.8%. It has a melting point of 36°–38° C.

(c) Preparation of isopropyl bis(3,4-dimethylphenyl) phosphinite

A solution of bis(3,4-dimethylphenyl) phosphinous chloride (11.5 g) in dry pentane (50 ml) was added dropwise to a stirred solution of isopropyl alcohol (2.52 g) and dry N,N-diethylaniline (6.26 g) in pentane (150 ml) at 0° C. over a period of 2 hours. The reaction was allowed to warm up to room temperature with stirring over a further 2 hours and was then left to stand at room temperature overnight. During the reaction N,N-diethylaniline hydrochloride precipitated out as a white solid; this was filtered off and washed with dry pentane (5×25 ml). Volatiles were removed from the combined filtrates under reduced pressure and the resulting pale yellow oil was fractionally distilled under reduced pressure.

Isopropyl bis(3,4-dimethylphenyl) phosphinite (8.5 g equivalent to 68.0% yield) distilled as a colourless liquid at 140°–148° C. and 0.15 mmHg pressure.

EXAMPLE 2

Preparation of isopropyl bis (3,4-dimethylphenyl) phosphinite (Grignard Route)

(a) Preparation of isopropylphosphordichloridite

Dry, degassed isopropylalcohol (120 g) was added dropwise with stirring over a period of 2 hours to phosphorus trichloride (32 g) at 0° C. The reaction was allowed to warm up to room temperature with stirring and was left to stand overnight. The reaction mixture was then fractionally distilled at atmospheric pressure.

Isopropylphosphordichloridite (105 g, equivalent to 32.5% yield based on isopropylalcohol) distilled as a colourless liquid at 126°–128° C.

(b) Preparation of 3,4-dimethylphenylmagnesium bromide

A solution of 3,4-dimethylbromobenzene (55.2 g) in dry, freshly distilled tetrahydrofuran (100 ml) was added dropwise with stirring over a period of 2 hours to Grignard grade magnesium turnings (8 g) which had been calcined at 200° C. in dry freshly distilled tetrahydrofuran (100 ml) the reaction being initiated by a single crystal of sublimed iodine. Dry, freshly distilled tetrahydrofuran (225 ml) was added dropwise at such a rate as to maintain the reaction at a reflux temperature. At the end of the reaction the Grignard reagent was filtered through dried glass-wool to remove unreacted magnesium turnings. Its strength was determined volumetrically by back titration with standard acid and alkali to be 0.68 molar (approximately 96.3% yield).

(c) Preparation of isopropyl bis(3,4-dimethylphenyl) phosphinite

A solution of 3,4-dimethylphenylmagnesium bromide Grignard reagent in tetrahydrofuran (425 ml) was added dropwise with stirring over a period of 2 hours to a solution of isopropylphosphordichloridite (23.12 g) in dry, freshly distilled tetrahydrofuran (100 ml) at 60° C. The reaction was then allowed to warm up to room temperature, with stirring, overnight. Dry pyridine (45.7 g) was then added, with stirring, and a white solid precipitated. After stirring for 1 hour the solvent was removed under reduced pressure and replaced by dry pentane (400 ml). Stirring was continued for a further 1 hour after which time the white solid was filtered off and washed with dry pentane (100 ml). Solvent was removed under reduced pressure from the combined filtrates and the resulting oil was fractionally distilled under reduced pressure.

Isopropyl bis(3,4-dimethylphenyl) phosphinite (34.49 g equivalent to a yield of 79.3%) distilled as a colourless liquid at 142°–150° C. and a pressure of 0.05 mmHg. It is noted that 'H n.m.r. indicated that 23% of this compound was isopropyl bis(2,3-dimethylphenyl) phosphinite, formed because commercial 3,4-dimethylbromobenzene contains 20–25% 2,3-dimethylbromobenzene as shown by 'H nmr.

EXAMPLE 3

Preparation of Isopropyl bis (3,4-tetralinyl) phosphinite (Friedel-Crafts Route)

(a) Preparation of 3,4-tetralinyl phosphonous dichloride

This was prepared by the method of Example 1(a) using the following quantities of reagents:
aluminium trichloride (67.5 g, 0.51 mole)

tetralin (50.3 g, 0.38 mole)
phosphorus trichloride (209 g, 1.52 mole)
phosphoryl chloride (77.6 g, 0.51 mole)

The reaction time was 6 hours. The 3,4-tetralinyl phosphonous dichloride distilled as a colourless liquid (53 g) at a pressure of 0.9 mmHg at 136° C. This was equivalent to a yield of 54%, based on tetralin.

(b) Preparation of bis(3,4-tetralinyl) phosphinous monochloride

This was prepared by the method of Example 1 (b) using the following quantities of reagents:
3,4-tetralinylphosphonous dichloride (46.2 g)
anhydrous zinc chloride (0.9 g)

The reaction was carried out for 12 hours at a temperature of 270°–290° C. and at a pressure of approximately 200 mmHg. Phosphorus trichloride (6.8 g) was evolved during the reaction. Unchanged starting material was distilled off as a colourless liquid, at 110° C. and a pressure of 0.1 mmHg. Product bis(3,4-tetralinyl)phosphinous monochloride was distilled as a colourless liquid, at 200° C. and a pressure of 0.1 mmHg. The product weighed 3.23 g, equivalent to a yield of 5% based on a conversion of 97.7%.

(c) Preparation of Isopropyl bis(3,4-tetralinyl) phosphinite

A solution of bis(3,4-tetralinyl) phosphinous monochloride (4.1 g) in pentane (25 ml) was added dropwise over 2 hours to an excess of an ice-cooled solution of isopropanol (1 ml) and diethylaniline (1 ml) in pentane (25 ml). Work-up was as described in Example 1(c). Product iso-propylbis(3,4-tetralinyl) phosphinite was distilled as a colourless liquid at 200°–210° C. at a pressure of 0.005 mmHg. The products weighed 1.74 g, equivalent to a yield of 40%.

EXAMPLE 4

Preparation of Isopropyl bis(3,4,5-trimethylphenyl) phosphinite (Friedel-Crafts Route)

(a) Preparation of 3,4,5-trimethylphenyl phosphonous dichloride

This was prepared by the method of Example 1 (a) using the following quantities of reagents:
aluminium trichloride (73.7 g, 0.55 mole)
1,2,3-trimethylbenzene (50.0 g, 0.42 mole)
phosphorus trichloride (228 g, 1.66 mole)
phosphoryl chloride (84.9 g, 0.55 mole)

The reaction time was 3 hours. The 3,4,5-trimethylphenyl phosphonous dichloride distilled as a pale yellow liquid (54 g) at a pressure of 0.8 mmHg at 115°–120° C. The liquid formed colourless crystals on standing (m.p. 53°–54° C.). This was equivalent to a yield of 59% based on 1,2,3-trimethylbenzene.

(b) Preparation of bis(3,4,5- trimethylphenyl) phosphinous monochloride

This was prepared by the method of Example 1 (b) using the following quantities of reagents:
3,4,5-trimethylphosphonous dichloride (51.8 g, 0.24 mole)
anhydrous zinc chloride (2.6 g, 5% by weight)

The mixture was heated for 7 hours at a temperature of 260°–290° C. in a distillation apparatus fitted with a heated fractionating head (120° C.). The reaction was carried out at a reduced pressure of 200 mmHg, and the evolved phosphorus trichloride was trapped using liquid nitrogen. The pressure was then reduced to 1.0 mmHg, unchanged starting material distilled off at 115°–120° C. and bis(3,4,5-trimethylphenyl) phosphinous monochloride distilled as a colourless liquid (8.2 g) at 152°–155° C. at a pressure of 0.01 mmHg. The liquid formed colourless crystals on standing. This was equivalent to a yield of 12% based on the dichloride.

(c) Preparation of Isopropyl bis(3,4,5-trimethylphenyl) phosphinite

A solution of bis(3,4,5-trimethylphenyl) phosphinous monochloride (8.2 g, 0.03 mole) in dry tetrahydrofuran (30 ml) was added dropwise with stirring over one hour to an ice-cooled solution of isopropanol (1.6 g, 0.03 mole), diethylaniline (3.7 g, 0.03 mole) and pentane (100 ml). Work-up was as described in Example 1 (c). Product isopropyl bis(3,4,5-trimethylphenyl) phosphinite was distilled as a colourless liquid at 135°–170° C. at a pressure of 0.005 mmHg. The products weighed 6.6 g, equivalent to a yield of 74% based on the monochloride.

EXAMPLES 5, 6 and 7

Dimerisation of Acrylonitrile

Acrylonitrile and isopropanol used in the following Examples were dried by adding calcium hydride powder to them and allowing them to stand overnight. The liquid was then decanted on to fresh calcium hydride powder and refluxed for 30 minutes. After this time the liquid was distilled from the calcium hydride into a vessel containing 4A molecular sieve for storage until required. Toluene was dried by refluxing it in the presence of sodium/potassium alloy and benzophenone until the blue/violet ketyl formed. The toluene was then distilled into a vessel containing 4A molecular sieve for storage until required.

In each case the final water level of the dried solvent was less than 15 ppm by volume, as determined by Karl Fisher titration procedure.

Three portions each of acrylonitrile (3 ml), isopropanol (1 ml) and toluene (10 ml) were mixed separately under an atmosphere of nitrogen.

To the three mixtures were added, in turn: Isopropyl bis(3,4-dimethylphenyl)phosphinite (100 mg), catalyst A, isopropyl bis(3,4-tetralinyl)phosphinite (100 ml), catalyst B, isopropyl bis(3,4,5-trimethylphenyl)phosphinite, catalyst C and, by way of comparison, isopropyl bistolyl phosphinite (100 mg), catalyst D, (prepared by a process analogous to that of Example 1, with toluene in place of o-xylene). The four mixtures were then heated to 60° C. and maintained at that temperature for 3 hours. At the end of this time, water was added to terminate the dimerisation reaction and the solid polymeric by-products filtered off. These are reported below as "hexamer." Solvents and unreacted acrylonitrile were removed by vacuum distillation, and the residue was weighed and analysed by gas-liquid chromatography, using adiponitrile as an internal standard. The results are given below in Table 1.

TABLE 1

| Ex No | Catalyst | % Conversion | % 1,4-DCB | % Hexamer |
|---|---|---|---|---|
| 5 | A | 43 | 90 | 1 |
| 6 | B | 27 | 88 | 1 |
| 7 | C | 60 | 88 | 2 |
| — | D | 19 | 88 | 2 |

1,4-DCB = 1,4 dicyanobutene

The % conversion indicates the % by weight of acrylonitrile (ACN) converted to total dimeric and polymeric products; the % 1,4-DCB or % hexamer is the weight of that product calculated as a % of the weight of ACN converted.

It will be seen from the above results that all catalysts gave a dimeric product having a very high proportion of linear dimer; but the compounds of the present invention (Examples 5, 6 and 7) gave a higher conversion and only half of the hexamer by-product (in the case of Examples 5 and 6) compared with comparative Example using catalyst D. Without prejudice to the invention it is thought that this is due to the fact that when toluene is used in place of o-xylene, tetralin or 1,2,3-trimethyl benzene in the procedure of Example 1, a mixed phosphinite is formed, i.e. a mixture of isopropyl bis(3-tolyl) phosphinite and isopropyl bis(4-tolyl) phosphinite, only one form being active as a catalyst. In the case of the tolyl catalyst, this can only be avoided by proceding via the more expensive Grignard route, whereas the very active xylyl, tetralinyl and trimethylphenyl catalysts may be prepared via the cheaper Friedel-Crafts route.

What we claim is:

1. As new compounds: phosphinites and phosphonites of general formula:

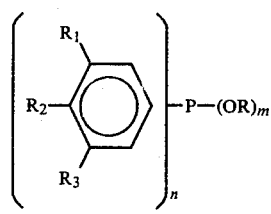

where $R_2$ is an electron-donating substituent, $R_1$ and $R_3$ are electron-donating substituents or hydrogen atoms, provided that they are not both hydrogen atoms, or either $R_1$ or $R_3$ forms part of a fused alicyclic ring with $R_2$, R is alkyl or cycloalkyl, and n and m are integers, each being either 1 or 2, provided that (m+n) equals 3, and when n is 2, the substituents on each aromatic ring may be the same or different.

2. Phosphinites and phosphonites as claimed in claim 1 wherein the electron-donating substituents $R_1$, $R_2$ and $R_3$ are selected from alkoxy, alkyl and alkylamino groups.

3. Phosphinites and phosphonites according to claim 2 wherein the alkoxy, alkyl and alkylamino groups contain from 1 to 8 carbon atoms.

4. Phosphinites and phosphonites as claimed in claim 3 wherein the alkoxy groups are selected from methoxy, ethoxy, iso-propoxy and tertiary-butoxy; the alkyl groups are selected from methyl, ethyl and propyl; and the alkylamino groups are selected from dimethylamino and diethylamino.

5. Phosphinites and phosphonites as claimed in any one of claims 1 to 4 wherein the groups R are alkyl or cycloalkyl groups containing from 1 to 10 carbon atoms.

6. Phosphinites and phosphonites as claimed in claim 5 wherein the alkyl groups R are selected from methyl, ethyl, isopropyl, neopentyl, 2-ethylhexyl and the cycloalkyl group R is cyclohexyl 7. Phosphinites and phosphonites as claimed in claim 1 wherein $R_1$ or $R_3$ forms part of a fused alicyclic ring with $R_2$ to give a tetralinyl group.

8. Isopropyl bis(3,4-dimethylphenyl) phosphinite, isopropyl bis(3,4-tetralinyl) phosphinite, isopropyl bis(3,4,5-trimethylphenyl) phosphinite.

9. Phosphinites and phosphonites on the general formula:

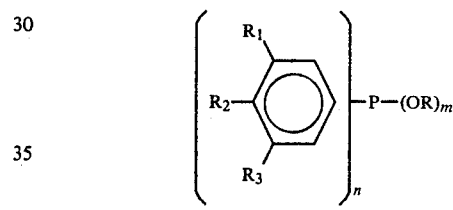

wherein:
$R_1$, $R_2$ and $R_3$ are electron donating substituents selected from the group consisting of alkoxy, alkyl and alkylamino groups, or either $R_1$ or $R_3$ forms part of a fused alicyclic ring with $R_2$ to give a tetralinyl group;
R is an alkyl or cycloalkyl group containing from 1 to 10 carbon atoms; and
n and m are integers each being either 1 or 2, provided that (M+n) equals 3, and when n is 2, the substituents on each aromatic ring may be the same or different.

* * * * *